(12) United States Patent
Hubbell et al.

(10) Patent No.: US 7,241,730 B2
(45) Date of Patent: Jul. 10, 2007

(54) ENZYME-MEDIATED MODIFICATION OF FIBRIN FOR TISSUE ENGINEERING: FIBRIN FORMULATIONS WITH PEPTIDES

(75) Inventors: Jeffrey A. Hubbell, Zumikon (CH); Jason C. Schense, Zurich (CH); Shelly E. Sakiyama, Zurich (CH)

(73) Assignees: Universitat Zurich, Zurich (CH); Eidgenossische Technische Hochschule Zurich, Zurich (CH)

( * ) Notice: Subject to any disclaimer, the term of this patent is extended or adjusted under 35 U.S.C. 154(b) by 639 days.

(21) Appl. No.: 10/106,804

(22) Filed: Mar. 25, 2002

(65) Prior Publication Data

US 2003/0119186 A1 Jun. 26, 2003

Related U.S. Application Data

(63) Continuation of application No. 09/141,770, filed on Aug. 27, 1998, now abandoned.

(51) Int. Cl.
*A01N 37/18* (2006.01)
(52) U.S. Cl. ............................. 514/2; 530/324; 424/193
(58) Field of Classification Search .................... 514/2; 530/324; 424/193
See application file for complete search history.

(56) References Cited

U.S. PATENT DOCUMENTS

| | | | |
|---|---|---|---|
| 4,613,665 A | 9/1986 | Larm | |
| 4,810,784 A | 3/1989 | Larm | |
| 4,894,436 A * | 1/1990 | Auerswald et al. | 530/324 |
| 5,032,573 A * | 7/1991 | Auerswald et al. | 514/12 |
| 5,100,668 A | 3/1992 | Edelman et al. | |
| 5,171,670 A | 12/1992 | Kronenberg et al. | |
| 5,202,247 A | 4/1993 | Kilburn et al. | |
| 5,258,302 A * | 11/1993 | Vedvick et al. | 435/254.23 |
| 5,428,014 A | 6/1995 | Labroo et al. | |
| 5,549,904 A * | 8/1996 | Juergensen et al. | 424/423 |
| 5,582,862 A | 12/1996 | Reed | |
| 5,591,603 A * | 1/1997 | Bjørn et al. | 435/69.2 |
| 5,641,670 A | 6/1997 | Treco et al. | |
| 5,651,982 A | 7/1997 | Marx | |
| 5,693,341 A | 12/1997 | Schroeder et al. | |
| 5,773,577 A | 6/1998 | Capello | |
| 5,840,837 A | 11/1998 | Krstenansky et al. | |
| 6,054,122 A | 4/2000 | MacPhee et al. | |
| 6,117,425 A | 9/2000 | MacPhee et al. | |
| 6,197,325 B1 | 3/2001 | MacPhee et al. | |
| 6,331,422 B1 | 12/2001 | Hubbell et al. | |
| 6,559,119 B1 | 5/2003 | Burgess et al. | |

FOREIGN PATENT DOCUMENTS

| | | |
|---|---|---|
| EP | 0 732 105 | 9/1996 |
| EP | 0 838 219 | 4/1998 |
| WO | WO 89/00051 | 1/1989 |
| WO | WO 90/05177 | 5/1990 |
| WO | WO 92/02620 | 2/1992 |
| WO | WO 92/09301 | 6/1992 |
| WO | WO 92/22312 | 12/1992 |
| WO | WO 94/20133 | 9/1994 |
| WO | WO 95/05396 | 2/1995 |
| WO | WO 95/23611 | 9/1995 |
| WO | WO 96/16983 | 6/1996 |
| WO | WO 96/17633 | 6/1996 |
| WO | WO 98/12228 | 3/1998 |
| WO | WO 99/08717 | 2/1999 |
| WO | WO 99/21588 | 5/1999 |

OTHER PUBLICATIONS

Webb. Enzyme Nomenclature. 1984. p. 177.*
Besson, et al. "Synthetic peptide substrates for a conductimetric assay of *Pseudomonas aeruginosa* elastase," *Analytical Biochemistry* 237(0232):216-223 (1996).
Blaschuk, et al., "Identification of a cadherin cell adhesion recognition sequence," *Dev. Biol* 139(1):227-229 (1990).
Borrajo, et al., "Derivatized Cyclodextrins as peptidometics: Influence on Neurite Growth," *Bioorganic and Medicinal Chemistry Letters* 7:1185-90 (1997).
Chuah, et al., "Differentiation and survival of rat olfactory epithlial neurons in dissociated cell culture," *Dev Brain Res* 60(2):123-132 (1991).

(Continued)

*Primary Examiner*—L Blaine Lankford
(74) *Attorney, Agent, or Firm*—Pabst Patent Group LLP

(57) ABSTRACT

Heparin-binding regions of several proteins, such as neural cell adhesion molecule, fibronectin, laminin, midkine, and anti-thrombin III have been shown to promote neurite extension on two-dimensional surfaces. The effect of heparin-binding peptides on neurite extension through three-dimensional matrices was investigated by culturing embryonic chick dorsal root ganglia (DRG) within fibrin gels containing chemically attached heparin-binding peptide (HBP). The length of neurites within fibrin gels containing cross-linked HBP was increased by more than 70% over extension through fibrin gels containing no peptide. The HBP sequence of antithrombin III was incorporated into the fibrin gel as the C-terminal domain of a bidomian, chimeric peptide; the N-terminal second domain of this peptide contained the $\forall$2-plasmin inhibitor substrate for Factor XIIIa. Factor XIIIa, a transglutaminase, was used to chemically attach the HBP-containing chimeric peptide to the fibrin gels during polymerization. The amount of HBP cross-linked into the fibrin gels was determined, after degradation by plasmin using gel permeation chromatography, to be approximately 8 moles of peptide per mole fibrinogen. A peptide (HBP), where the cross-linking glutamine was replaced with glycine, showed no increase in extension in comparison with fibrin gels. The additional of heparin to the gel percursors resulted in no increase in neurite extension in comparison with fibrin gels. HBPs promote neurite extension by binding to cell surface proteoglycans on the DRG.

12 Claims, 5 Drawing Sheets

OTHER PUBLICATIONS

Coombs, et al. "Directing sequence-specific proteolysis to new targets. The influence of loop size and target sequence on selective proteolysis by tissue-type plasminogen activator and urokinase-type plasminogen activator," *J. Biol. Chem.* 273(8):4323-8 (1998).

Dimilla, et al., "Mathematical model for the effects of adhesion and mechanics on cell migration speed," *Biophys. J.* 60(1):15-37 (1991).

Dinbergs, et al., "Cellular response to transforming growth factor-beta1 and basic fibroblast growth factor depends on release kinetics and extracellular matrix interactions," *J. Biol. Chem.* 271(47):29822-9 (1996).

Edelman, et al., "Basic fibroblast growth factor enhances the coupling of intimal hyperplasia and proliferation of vasa vasorum in injured rat arteries," *J. Clin. Invest.* 89(2):465-73 (1992).

Edelman, et al., "Controlled and modulated release of basic fibroblast growth factor," *Biomaterials.* 12(7):619-26 (1991).

Edelman, et al., "Perivascular and intravenous administration of basic fibroblast growth factor: vascular and solid organ deposition," *Proc. Natl. Acad. Sci. U. S. A.* 90(4):1513-7 (1993).

Edgar, et al., "The heparin-binding domain of laminin is responsible for its effects on neurite outgrowth and neuronal survival," *EMBO J.* 3(7):1463-8 (1984).

Fowlkes, et al., "Characterization of gylcosaminoglycan-binding domains present in insulin-like growth factor-binding protein-3," *J Biological Chemistry* 271(25):14676-9 (1996).

Götz, et al., "Neurotrophin-6 is a new member of the nerve growth factor family," *Nature* 372(6503):266-9 (1994).

Harada, et al., "Basic fibroblast growth factor improves myocardial function in chronically ischemic porcine hearts," *J. Clin. Invest.* 94(2):623-30 (1994).

Hata, et al., "Binding of lipoprotein lipase to heparin. Identification of five critical residues in two distinct segments of the amino-terminal domain," *J. Biol. Chem.* 268(12):8447-57 (1993).

Haugen, et al, "Central and peripheral neurite outgrowth differs in preference for heparin-binding versus integrin-binding sequences," *J. Neurosci.* 12(6):2034-42 (1992).

Herbert, et al., "Effects of fibinolysis on neurite growth from dorsal root ganglia cultured in two- and three-dimensional fibrin gels," *J. Comp. Neurol.* 365(3):380-91 (1996).

Herbert, et al., "Effects of fibrin micromorphology on neurite growth from dorsal root ganglia cultured in three-dimensional fibrin gels," *J. Biomed. Mater. Res.* 40(4):551-9 (1998).

Kallapur, et al., "The neural cell adhesion molecule (NCAM) heparin binding domain binds to cell surface heparan sulfate proteoglycans," *J. Neurosci. Res.* 33(4):538-48 (1992).

Kaneda, et al., "Midkine, a heparin-binding growth/differentiation factor, exhibits nerve cell adhesion and guidance activity for neurite outgrowth in vitro," *J. Biochem.* 119(6):1150-6 (1996).

Kiguchi, et al., "Altered expression of epidermal growth factor receptor ligands in tumor promoter-treated mouse epidermis and in primary mouse skin tumors induced by an initiation-promotion protocol," *Mol. Carcinog.* 22(2):73-83 (1998).

Kinosaki, et al., "Identification of heparin-binding stretches of a naturally occurring deleted variant of hepatocyte growth factor (dHGF)," *Biochim. Biophys. Acta.* 1384(1):93-102 (1998).

Kleinman, et al., "The laminins: a family of basement membrane glycoproteins important in cell differentiation and tumor metastases," *Vitam. Horm.*47:161-86 (1993).

Kleinman, et al., *Vitamins and Hormones* 47:10-93 (1993).

Lopez, et al., "Basic fibroblast growth factor in a porcine model of chronic myocardial ischemia: a comparison of anaiographic, echocardiographic and coronary flow parameters," *J. Pharmacol. Exp. Ther.* 282(1):385-90 (1997).

Lopez, et al., "Local perivascular administration of basic fibroblast growth factor: drug delivery and toxicological evaluation," *Drug Metab. Dispos.* 24(8):922-4 (1996).

Martin & Timpl, "Laminin and other basement membrane components," *Annu. Rev. Cell. Biol.* 3:57-85 (1987).

Massia, et al., "An RGD spacing of 440 nm is sufficient for integrin alpha V beta 3-mediated fibroblast spreading and 140 nm for focal contact and stress fiber formation," *J. Cell. Biol.* 114(5):1089-110 (1991).

McCaffrey, et al., "Transforming growth factor-beta 1 is a heparin-binding protein: identification of putative heparin-binding regions and isolation of heparins with varying affinity for TGF-beta 1," *J. Cell. Physiol.* 152(2):430-40 (1992).

Netzel-Arnett, et al., "Sequence specificities of human fibroblast and neutrophil collagenases," *J. Biol. Chem.* 266(11):6747-55 (1991).

Nolo, et al., "Developmentally regulated neurite outgrowth response from dorsal root ganglion neurons to heparin-binding growth-associated molecule (HB-GAM) and the expression of HB-GAM in the targets of the developing dorsal root ganglion neurites," *Eur. J. Neurosci.* 8(8):1658-65 (1996).

Presta, et al., "Structure-function relationship of basic fibroblast growth factor: site-directed mutagenesis of a putative heparin-binding and receptor-binding region," *Biochem. Biophys. Res. Commun.* 185(3):1098-107 (1992).

Rogers, et al., "Neuron-specific interactions with two neurite-promoting fragments of fibronectin," *J. Neurosci.* 5(2):369-78 (1985).

Schense, et al., "Cross-linking exogenous bifunctional peptides into fibrin gels with factor XIIIa," Bioconjugate Chemistry 10:75-81 (1998).

Schroeder-Teft, et al., "Collagen and heparin matrices for growth factor delivery," *J Controlled Release* 49:291-298 (1997).

Sellke, et al., "Basic FGF enhances endothelium-dependent relaxation of the collateral-perfused coronary microcirculation," *Am. J. Physiol.* 267(4 Pt 2):H1303-11 (1994).

Smith, et al., "Rapid identification of highly active and selective substrates for stromelysin and matrilysin using bacteriophage peptide display libraries," *J. Biol. Chem.* 270(12):6440-9 (1995).

Spillman, et al., "Defining the interleukin-8-binding domain of heparan sulfate," *J. Biol. Chem.* 273(25):15487-93 (1998).

Steffen, et al., "Characterization of cell-associated and soluble forms of connective tissue growth factor (CTGF) produced by fibroblast cells in vitro," *Growth Factors* 15(3):199-213 (1998).

Studier, et al., "Use of T7 RNA polymerase to direct expression of clones genes," *Methods Enzymol.* 185:60-89 (1990).

Takagi, et al., "Amino acid sequence studies on the alpha chain of human fibrinogen. Location of four plasmin attack points and a covalent cross-linking site," *Biochemistry* 14(23):5149-56 (1975).

Tashiro, et al., "A synthetic peptide containing the IKVAV sequence from the A chain of laminin mediates cell attachment, migration, and neurite outgrowth," *J. Biol. Chem.* 264(27):16174-82 (1989).

Tessler, et al., "Heparin modulates the interaction of VEGF165 with soluble and cell associated flk-1 receptors," *J. Biol. Chem.* 269(17):12456-61 (1994).

Tyler-Cross, et al., "Heparin binding domain peptides of antithrombin III: analysis by isothermal titration calorimetry and circular dichroism spectroscopy," *Protein Sci.* 3(4):620-7 (1994).

Yamada, "Adhesive recognition sequences," *J. Biol. Chem.* 266(20):12809-12 (1991).

Yanish-Perron, et al., "Improved M13 phage cloning vectors and host strains: nucleotide sequences of the M13mp18 and pUC19 vectors," *Gene.* 33(1):103-19 (1985).

Zucker & Katz, "Platelet factor 4: production, structure, and physiologic and immunologic action," *Proc. Soc. Exp. Biol. Med.* 198(2):693-702 (1991).

Baumgartner, et al., "Constitutive expression of phVEGF165 after intramuscular gene transfer promotes collateral vessel development in patients with critical limb ischemia," *Circulation* 97:1114-1123 (1998).

Blaess, et al., "Structural analysis of the sixth immunoglobulin-like domain of mouse neural cell adhesion molecule L1 and its interactions with $\alpha_v\beta_3$, $\alpha IIb\beta_3$, and $\alpha 5\beta 1$ integrins," *J Neurochem* 71:2615-2625 (1998).

Brooks, et al., "Requirement of vascular integrin $\alpha_v\beta_3$ for angiogenesis," *Science* 264:569-571 (1994).

Camarata, et al., "Sustained Release of Nerve Growth Factor from Biodegradable Polymer Microspheres," *Neurosurgery* 30(3) 313-319 (1992).

Cardin, et al., "Molecular Modeling of Protein-Glycosaminoglycan Interactions," *Arteriosclerosis* 9:21-32 (1989).

Dedhar & Hannigan, "Integrin cytoplasmic interactions and bidirectional transmembrane signaling," *Current Opinion in Cell Biology* 8:657-669 (1996).

Downs, et al., "Calcium Alginate Beads as a Slow-Release System for Delivering Angiogenic Molecules in Vivo and In Vitro," *Journal of Cellular Physiology* 152:422-429 (1992).

Fasol, et al., "Experimental use of a modified fibrin glue to induce site-directed angiogenesis from the aorta to the heart," Journal of Thoracic and Cardiovascular Surgery 107:1432-9 (1994).

Felding-Habermann, et al., "A single immunoglobulin-like domain of the human neural cell adhesion molecule L1 supports adhesion by multiple and platelet integrins," *J Cell Biol* 139:1567-1581 (1997).

Folkman, "Angiogenesis in cancer, vascular, rheumatoid and other disease," *Nature Medicine* 1:27-31 (1995).

Grainger, et al., "Poly(dimethylsiloxane)-poly(ethylene oxide)-heparin block copolymers. I. Synthesis and characterization" *J. Biomed. Mater. Res.* 22(3):231-249 (1988).

Griesler, et al., "Enhanced endothelial of expanded polyethrafluoroethylene grafts by fibroblast growth factor type 1 pretreatment," *Surgery* 112:244-255 (1992).

Hall, et al., "Molecular properties of fibrin-based matrices for promotion of angiogenesis in vitro" *Microvascular Research* 62:315-326 (2001).

Houle & Johnson, "Nerve growth factor (NGF)-treated nitrocellulose enhances and directs the regeneration of adult rat dorsal root axons through intraspinal neural tissue transplants," *Neuroscience Letters* 103:17-23 (1989).

Humphries, "Integrin activation: the link between ligand binding and signal transduction," *Curr Opin Cell Biol* 8:632-640 (1996).

Ilan, et al., "Distinct signal transduction pathways are utilized during the tube formation and survival phases of in vitro angiogenesis," *J of Cell Science* 111:3621-3631 (1998).

Inger & Folkman, "How does extracellular matrix control capillary morphogenesis?" Cell 58:803-805 (1989).

Kang, et al., "Selective stimulation of endothelial cell proliferation with inhibition of smooth muscle cell proliferation by fibroblast growth factor-1 plus heparin delivered from glue suspensions," *Surgery* 118:280-287 (1995).

Lee, et al., "Analysis of affinity and structural selectivity in the binding of proteins to glycosaminoglycans: Development of a sensitive electrophoretic approach," *Biochemistry* 88:2768-2772 (1991).

Lin, et al., "Purification and Initial Characterization of Rat B49 Glial Cell Line-Derived Neurotrophic Factor," *Journal of Neurochemistry* 758-768 (1994).

Lorsordo, et al., "Gene therapy for myocardial angiogenesis. Initial clinical results with direct myocardial injection of phVEGF165 as sole therapy for myocardial ischemia," *Circulation* 98:2800-2804 (1998).

Lyon, et al., "The Interaction of the Transforming Growth-Factor-ÿs with Heparin/Heparan Sulfate is Isoform-specific," *The Journal of Biological Chemistry* 272(29):18000-18006 (1997).

Maysinger, et al., "Microencapsulated nerve growth factor: effects on the forebrain neurons following devascularizing cortical lesions," *Neuroscience Letters* 140:71-74 (1992).

Montgomery, et al., "Human neural cell adhesion molecule L1 and Rat homologue NILE are ligands for integrin □□□3," *J Cell Biol* 132:475-485 (1996).

Nehls & Herrmann, "The configuration of fibrin clots determine capillary morphogenesis and endothelial cell migration," *Microvascular Research* 51:347-364 (1996).

Pepper, et al., "Angiogenesis: a paradigm for balanced extracellular proteolysis cell migration and morphogenesis," *Enzyme Protein* 49:138-162 (1996).

Powell, et al., "Controlled Release of nerve growth factor from a polymeric implant," *Brain Research* 515:309-311 (1990).

Reddi, "Role of Morphogeneti c Proteins in Skeletal Tissue Engineering and Regeneration," *Nature Biotechnology* 16:247-252 (1998).

Rixon, et al., "Do the non-catalytic polysaccharide-binding domains and linker regions enhance the biobleaching properties of modular xylanases?" *Appl. Microbiol. Biotechnol.* 46(5-6):514-520 (1996).

Ruoslahti & Engvall, "Perspectives series: Cell adhesion in vascular biology," *J Clin Invest* 99:1149-1152 (1997).

Sakata & Aoki, et al., "Cross-linking if □2-plasmin inhibitor to fibrin by fibrin-stabilizing factor," *J Clin Invest* 65:290-297 (1980).

Schumacher, et al., "Induction of neoangiogenesis in ischemic myocardium by human growth factors," *Circulation* 97:645-650 (1998).

Seibel, et al., "Transfection of mitochondria: strategy towards a gene therapy of mitochondrial DNA diseases" *Nucleic Acids Res.* 23(1):10-17 (1995).

Stein, et al., "Eph receptors discriminate specific ligand oligomers to determine alternative signaling complexes, attachment, and assembly responses," *Genes & Development* 12:667-678 (1998).

Takeshita, et al., "Therapeutic Angiogenesis. A single intraarterial bolus of vascular endothelial growth factor augments revascularization in a rabbit ischemic hind limb model," J Clin Invest 93:662-670 (1994).

Thompson, et al., "Site-directed ncovessel formation in vivo," *Science* 241:1349-1352 (1988).

Wang, et al., "Molecular distinction and angiogenesis interaction between embryonic arteries and veins revealed by ephrin-B2 and its receptod Eph-B4," *Cell* 93:741-753 (1998).

Weatherford, et al., "Vascular endothelial growth factor and heparin in a biologic glue promotes human aortic endothelial cell proliferation with aortic smooth muscle cell inhibition," *Surgery* 433-439 (1996).

\* cited by examiner

ENZYME-MEDIATED MODIFICATION OF FIBRIN FOR TISSUE ENGINEERING: FIBRIN FORMULATIONS WITH PEPTIDES

CROSS-REFERENCE TO RELATED APPLICATIONS

This application is a continuation of application Ser. No. 09/141,770, filed Aug. 27, 1998 now abandoned, entitled "Enzyme-Mediated Modification of Fibrin for Tissue Engineering: Fibrin Formulations with Peptides", by Jeffrey A. Hubbell, Jason C. Schense and Shelly E. Sakiyama.

FILED OF THE INVENTION

The present invention relates generally to the fields of materials useful in the support of tissue and cell incorporation and growth. More particularly, it concerns particular substrates of protein, such as fibrin, to which bioactive peptides and combinations of peptides are attached.

BACKGROUND OF THE INVENTION

The active domain of many proteins may in some cases be mimicked at least in part through the use of short peptide sequences derived from the active site of the protein (Massia and Hubbell, 1991, Yamada, 1991). Through this method, the activity of a specific protein can be conferred to an otherwise nonactive surface or matrix. This method allows a much higher concentration of active sequences to be immobilized onto a surface than is found naturally. While many peptides have been shown to have a monotonic correlation between density and cellular activity, other peptides are known to reach a maximum activity at a moderate level of peptide density. The best example is migration of cells on a surface coated with RGD (SEQ ID NO:2). If the concentration of RGD (SEQ ID NO:2) is too high, the surface binds too strongly to the cells, inhibiting cellular migration. However, if the RGD (SEQ ID NO:2) density is too low, then there is not enough traction for these cells to effectively migrate across the surface, leading to a maximal migration rate at a moderate surface concentration of peptide. (DiMilla, et al., 1991) Unfortunately, there is not very much research of the concentration dependent effect of these peptides in a three dimensional matrix. It is not possible to predict which peptides will show saturating behavior and it is not possible to predict at what peptide concentration maximal benefits will be observed.

While individual peptides can partially mimic the effect of the whole protein, the magnitude of this effect is typically lower. This is due to several reasons, including possible changes in conformation, peptide accessibility and changes in solubility between the peptide and the protein. One additional difference is that the interaction between cells and individual proteins or entire extracellular matrix involve simultaneously binding to multiple peptide sequences. (Martin, 1987, Kleinman, et al., 1993) Sometimes these sequences are on the same protein, but often they are on different proteins. In general it is not possible to predict which combinations might interact negatively, which might interact additively and which might interact synergistically.

Reports in the literature relate to findings that heparin-binding domains of proteins as well as receptor-mediated binding domains promote neuron adhesion and neurite extension. Many heparin binding domains have been identified (Table 1) and furthermore, haparin binding regions of several proteins such as neural cell adhesion molecule, fibronectin, laminin, midkine, and anti-thrombin III have been reported to promote neurite extension on two-dimensional surfaces. (Edgar, et al., 1984, Borrajo, et al., 1997, Kallapur and Akeson, 1992, Kaneda, et al., 1996, Rogers, et al., 1985) These heparin-binding domains have been reported by indirect evidence to interact with cell-surface proteoglycans by a number of methods including inhibition by soluble heparin, enzymatic removal of cell surface proteoglycans, and biochemical inhibition of proteoglycan synthesis (Kallapur and Akeson, 1992). These peptides have only been studies in 2-dimensional systems.

SUMMARY OF THE INVENTION

The present invention discloses a variety of particularly biologically active cell matrices to which a number of cell types may attach and grow. By way of example, the invention provides for protein matrices that have been modified to include chemically cross-linked peptides. These peptides may be defined as having a sequence that mimics heparin-binding regions of several proteins, such as neural cell adhesion molecule, fibronectin, laminen, midkine, and anti-thrombin III. These peptides are chemically cross-linked to protein and/or fibrin gels to provide particularly efficacious platforms for the attachment and extension of a variety of different cell types.

The protein matrices of the present invention may include a single or multiple peptide chemically cross-linked thereto. By way of example, one such peptide is HAV (SEQ ID NO:6). By way of example, the HAV (SEQ ID NO:6) peptide may be cross-linked into said fibrin gels of the present invention at a concentration of about 2 mol peptide/mol fibrin gel. Another peptide that may be employed with the matrices of the present invention is RGD (SEQ ID NO:2). By way of example, said peptide may be included in cross-linked fashion to the matrix at a concentration of about 1.5 mol RGD/peptide mol fibrin gel. Yet another peptide that may be included with the matrices of the invention is IKVAV (SEQ ID NO:1). An exemplary concentration of this peptide found efficacious by the present inventors was a concentration of about 8 mol peptide/mol fibrin gel. Other examples of peptides that may be used in the practice of the present invention are the peptide YIGSR (SEQ ID NO:3) and the peptide RNIAEIIKDI (SEQ ID NO:5). These particular peptides have been found to be particularly efficacious in the practice of the present invention when employed at a concentration of about 6 mol YIGSR (SEQ ID NO:3) peptide/mol fibrin gel and at a concentration of about 8 mol RNIAEIIKDI (SEQ ID NO:5) peptide/mol fibrin gel.

In another aspect, the present invention defines a protein matrix that include a mixture of at least two peptides. By way of example, said peptides may be further defined as peptide HAV (SEQ ID NO:6), IKVAV (SEQ ID NO:1), RNIAEIIKDI (SEQ ID NO:5), YIGSR (SEQ ID NO:3), DGEA (SEQ ID NO:4), a combination thereof, a combination of peptide fragments comprising HAV (SEQ ID NO:6), IKVAV (SEQ ID NO:1), RNIAEIIKDI (SEQ ID NO:5), YIGSR (SEQ ID NO:3), and DGEA (SEQ ID NO:4), or a fusion peptide comprising these peptides. By way of example, an embodiment of the invention may comprise a fibrin gel matrix that includes a mixture of peptides cross-linked thereto, this particular mixture of peptides being defined as comprising IKVAV (SEQ ID NO:1), RGD (SEQ ID NO:2), YIGSR (SEQ ID NO:3), and RNIAEIIKDI (SEQ ID NO:5), wherein the particular fibrin gel matrix is essentially free of HAV (SEQ ID NO:6) peptide. As used in the description of the present invention, the term "essentially free" is defined as essentially absent any concentration of the HAV (SEQ ID NO:6) peptide that would have a neurite extension inhibiting effect on neurite cells cross-linked to a fibrin gel.

In some embodiments, the invention may be defined as a protein gel that comprises a neurite extension promoting amount of a defined ratio of peptide HAV (SEQ ID NO:6) and peptide YIGSR (SEQ ID NO:3). A ratio of about 1 HAV (SEQ ID NO:6):3 YIGSR (SEQ ID NO:3) cross-linked into a protein gel matrix has been found by the present inventors to be particularly useful in the practice of the present invention. In yet another aspect, the protein gel may include a neurite extension promoting amount of a ratio of the peptide HAV (SEQ ID NO:6) and the peptide RNIAEIIKDI (SEQ ID NO:5). Where these are the two peptides of choice, they may be included at a ratio of about 1:3 as cross-linked to the protein gel. In yet other embodiments of the inventoin, the protein gel may include a first peptide RGD (SEQ ID NO:2) and a second peptide YIGSR (SEQ ID NO:3). Alternatively, the protein gel may comprise a ratio of the peptide RGD (SEQ ID NO:2) together with the peptide DGEA (SEQ ID NO:4). The ratio of these two peptides relative to one another that may be employed in the present invention is about 1:3.

In yet another aspect, the protein gel matrix of the present invention may include a mixture of 3 or more peptides. By way of example, a mixture of peptide RGD (SEQ ID NO:2), peptide YIGSR (SEQ ID NO:3), and peptide RNIAEIIKDI (SEQ ID NO:5) may be included in chemically cross-linked fashion to the protein gel, these three peptides to be included at a ratio of about 1:1:1, respectively.

All of the above protein and gel matrices may be further defined as three-dimensional matrices. Surprisingly, these three-dimensional matrices modified to include the peptides described herein have been found to advantageously provide enhanced and, in some cases synergistic enhancement of neurite cell growth and extension.

In some embodiments, the invention provides for fibrin gel matrices. These particular embodiments against comprising a neurite extension promoting ratio of a mixture of peptides. These peptides are again cross-linked to the fibrin gel. The particular matrices of the present invention may also comprise a protein gel other than fibrin. Some embodiments of the protein gel include cross-linked thereto a mixture of peptides as described above at a neurite extension promoting ratios.

The invention in yet another aspect provides for a bi-domain peptide. The bi-domain peptide in some embodiments may be defined as comprising a first domain of a heparin-binding domain and a second domain consisting essentially of a Factor XIIIa substrate or a bioactive peptide. The bi-domain in some particular embodiments may be further defined as comprising a first domain of a peptide K(βA)FAKLAARLYRKA (SEQ ID NO:8), YKKIIKKL (SEQ ID NO:9), KHKGRDVILKKDVR (SEQ ID NO:10), or a mixture thereof. Protein gels that include chemically cross-linked thereto the afore-described bi-domain peptides may thus also be provided according to the present invention.

Yet another aspect of the invention provides for fibrin that has been modified to include the bi-domain peptides as described herein. By way of example, the bi-domain peptide employed to modify fibrin may be further defined as comprising a heparin binding domain from ATIII (SEQ ID NO:18). The particular heparin-binding domain peptide that may be employed according to the present invention to modify a fibrin matrix or a cell matrix that includes at least in part fibrin may be defined as a heparin binding domain peptide that elutes from a heparin-affintiy column at [NaCl] >0.34 mol.

The various peptide modified fibrin matrices described herein may be further defined as a protein gel comprising cross-linked peptides. A protein gel that comprises a chemically bound protease inhibitor provides yet another embodiment of the present invention. By way of example, the protease inhibitor may be defined as a2-PI. The protease inhibitor may be even further defined as a modified aprotinin with a Factor XIIIa substrate site.

The protease inhibitor may be further defined as comprising a modified aprotinin, a Factor XIIIa substrate, and a protease degradation site. In some embodiments, the protease inhibitor may be further defined as comprising a modified aprotinin and a heparin-binding domain sequence. In yet other embodiments, the protease inhibitor may be defined as comprising a modified aprotinin having an hbd and a protease degradation site. The protein gel of the invention maybe further defined as comprising a peptide having a protease binding site covalently incorporated to said gel. The protease binding site in some embodiments of the invention may be further defined as an enzymatic cleavage site, this enzymatic cleavage site having a low kcat and a high km. In yet other embodiments, the protease binding site may be further defined as an enzymatic binding domain.

In yet another aspect, the present invention provides for three-dimensional matrices capable of supporting neurite cell extension. In some embodiments, the matrix may be defined as comprising a neurite cell extension promoting amount of a mixture of peptides, wherein each of said peptides comprise a sequence that defines a heparin-binding sequence. These three-dimensional matrices may be further defined as fibrin gels or protein gels. Where the three-dimensional matrix includes a mixture of peptides, these peptides may be further defined as having a sequence comprising a heparin-binding peptide of antithrombin II. The heparin-binding peptide will be chemically attached to said three-dimensional matrix, and may be particularly described as cross-linked to the matrix. Particular embodiments of the three-dimensional matrix of the invention may be further defined as comprising a fibrin gel. Where the peptide included within the three-dimensional matrix is a heparin-binding peptide, the peptide may be further defined as a sequence of antithrombin III.

In yet a further aspect, the invention provides for chimeric peptides. In some embodiments, the chimeric peptide comprises a first C-terminal domain comprising a heparin-binding peptide sequence of antithrombin III; and a second N-terminal domain comprising an a2-plasmin inhibitor substrate for Factor XIIIa. Three-dimensional matrices of protein and/or fibrin in particular, having chemically cross-linked thereto the afore-described chimeric peptides are also provided with the present invention. By way of example, a fibrin gel according to this embodiment may be further defined as comprising a neurite extension promoting amount of about 8 mols of the chimeric peptide/mol of fibrin.

SEQUENCE ID. TABLE

| (SEQ ID NO:) | SEQUENCE |
|---|---|
| 1 | IKVAV |
| 2 | RGD |
| 3 | YIGSR |
| 4 | DGEA |
| 5 | RNIAIEIIKDI |
| 6 | HAV |
| 8 | K(βA)FAKLAARLYRKA |
| 9 | YKKIIKKL |
| 10 | KHKGRDVILKKDVR |
| 11 | YEKPGSPPREVVPRPRPCV |
| 12 | KNNQKSEPLIGRKKT |
| 13 | KDPKRL |
| 14 | YRSRKY |
| 15 | YKKPKL |
| 16 | AKRSSKM |
| 17 | CRKRCN |
| 18 | *LNQEQVSP* K(βA)FAKLAARLYRKA |
| 19 | *LNQEQVSP* YKKIIKKL |
| 20 | *LNQEQVSP* KHKGRDVILKKDVR |

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Following long-standing patent law convention, the terms "a" and "an" mean "one or more" when used in this application, including the claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

TABLE 1

List of heparin binding peptides and the proteins they are derived from.

| Protein | Heparin-binding domain | Reference |
|---|---|---|
| Anti-thrombin III | K(βA)FAKLAARLYRKA (SEQ ID NO:8) | Tyler-Cross et al., 1994 |
| Platelet Factor 4 | YKKIIKKL (SEQ ID NO:9) | Zeuker and Katz, 1991 |
| Neural Cell Adhesion Molecule | KHKGRDVILKKDVR (SEQ ID NO:10) | Kallapur, 1992 |
| Fibronectin | YEKPGSPPREVVPRPRPCV (SEQ ID NO:11) KNNQKSEPLIGRKKT (SEQ ID NO:12) | Haugen, et al, 1992 |
| bFGF | KDPKRL (SEQ ID NO:13) YRSRKY (SEQ ID NO:14) | SwissProt: P09038 |
| aFGF | YKKPKL (SEQ ID NO:15) | SwissPROT: P05230 |
| LPL | AKRSSKM (SEQ ID NO:16) CRKRCN (SEQ ID NO:17) | Hata, et al., 1993 |

EXAMPLE 1

Figure 1:
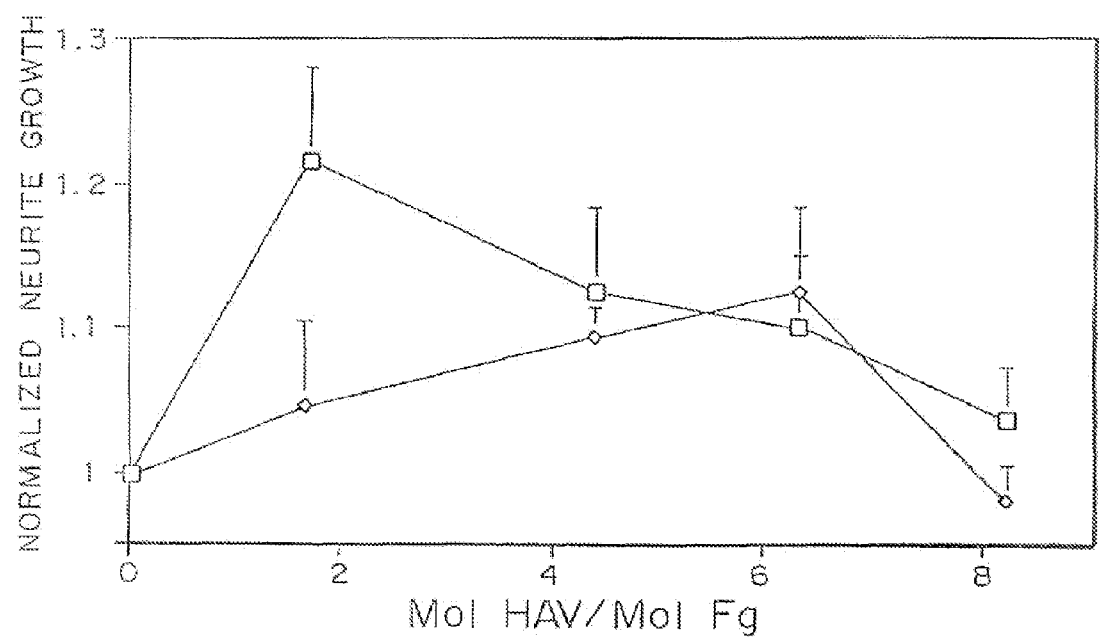
FIG. 1 Enhancement of neurite outgrowth with HAV (SEQ ID NO:6) modified fibrin gels. A concentration series of HAV (SEQ ID NO:6) cross-linked into fibrin was tested in triplicate with day 8 chick dorsal root ganglia. The level of growth at 24 and 48 hours was calculated and normalized to growth in unmodified fibrin. Mean and standard error of the mean are shown. Legend to FIG. 1: -□- 24 Hours, -◇- 48 Hours.
Figure 2:
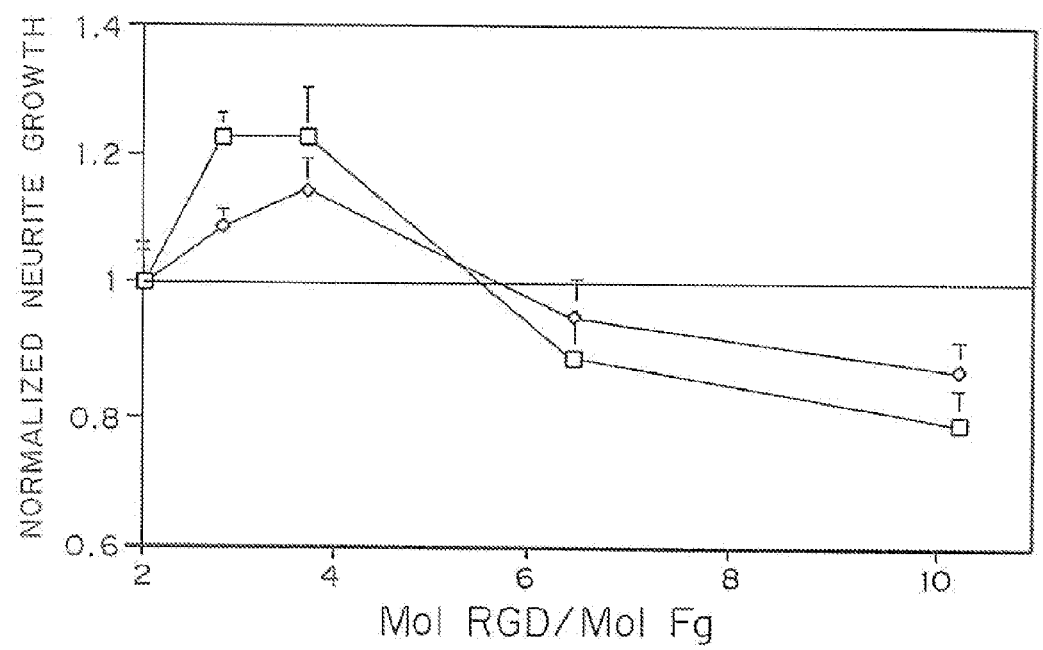
FIG. 2 Enhancement of neurite outgrowth with RGD (SEQ ID NO:2)-modified fibrin gels. A concentration series of RGD (SEQ ID NO:2) cross-linked into fibrin was tested in triplicate with day 8 chick dorsal root ganglia. (because fibrin naturally contains two active RGD (SEQ ID NO2) sites, the level of incorporation of RGD (SEQ ID NO:2) becomes 2-10 mol RGD (SEQ ID NO:2)/mol fg instead of 0-8) The level of growth at 24 and 48 hours was calculated and normalized to growth in unmodified fibrin. Mean and standard error of the mean are shown. Legend to FIG. 2: -□- 24 Hour Data, -◇- 48 Hour Data.
Figure 3:
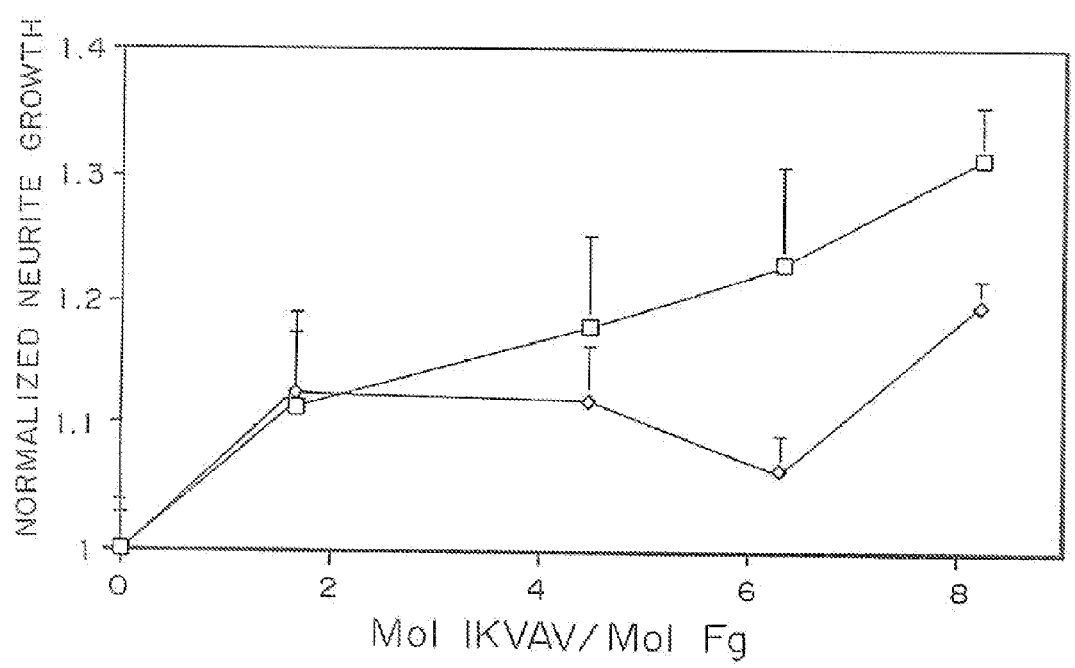
FIG. 3 Enhancement of neurite outgrowth with IKVAV (SEQ ID NO:1)-modified fibrin gels. A concentration series of IKVAV (SEQ ID NO:1) cross-linked into fibrin was tested in triplicate with day 8 chick dorsal root ganglia. The level of growth at 24 and 48 hours was calculated and normalized to growth in unmodified fibrin. Mean and standard error of the mean are shown. Legend to FIG. 3: -□- 24 Hours, -◇- 48 Hours FIG. 4 Enhancement of neurite outgrowth with RNIAEIIKDI (SEQ ID NO:5) modified fibrin gels. A concentration series of RNIAEIIKDI (SEQ ID NO:5) cross-linked into fibrin was tested in triplicate with day 8 chick dorsal root ganglia. The level of growth at 24 and 48 hours was calculated and normalized to growth in unmodified fibrin. Mean and standard error of the mean are shown. Legend to FIG. 4: -□- 24 Hours, -◇- 48 Hours FIG. 5 Enhancement of neurite outgrowth with YIGSR (SEQ ID NO:3) modified fibrin gels. A concentration series of YIGSR (SEQ ID NO:3) cross-linked into fibrin was tested in triplicate with day 8 chick dorsal root ganglia. The level of growth at 24 and 48 hours was calculated and normalized to growth in unmodified fibrin. Mean and standard error of the mean are shown. Legend to FIG. 5: -□- 24 Hours, -◇- 48 Hours FIG. 6 Peptides were grafted in combination at a total concentration of 8 mol peptide/mol fg. HAV (SEQ ID NO:6) demonstrated a maximum efficacy at 2 mol/mol fg. Therefore, HAV (SEQ ID NO:6) was incorporated at this concentration and the second peptide shown was incorporated at 6 mol/mol fg. The growth of neurites relative to growth in unmodified fibrin is shown in the first bars of this graph. The normalized growth of the second peptide grafted alone is shown as well as the theoretical additive growth derived from the two peptides grafted alone. Mean and standard error of the mean are shown. Legend to FIG. 6: □ Combination Growth, ▧ Growth Alone, ▨ Additive Results from Growth Alone.
Figure 4:
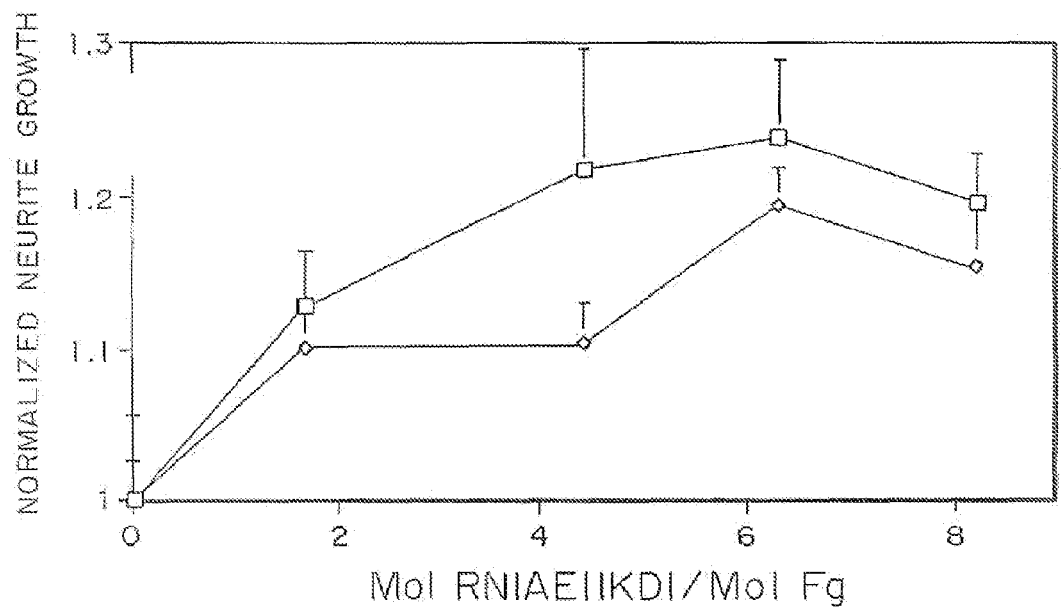
Figure 5:
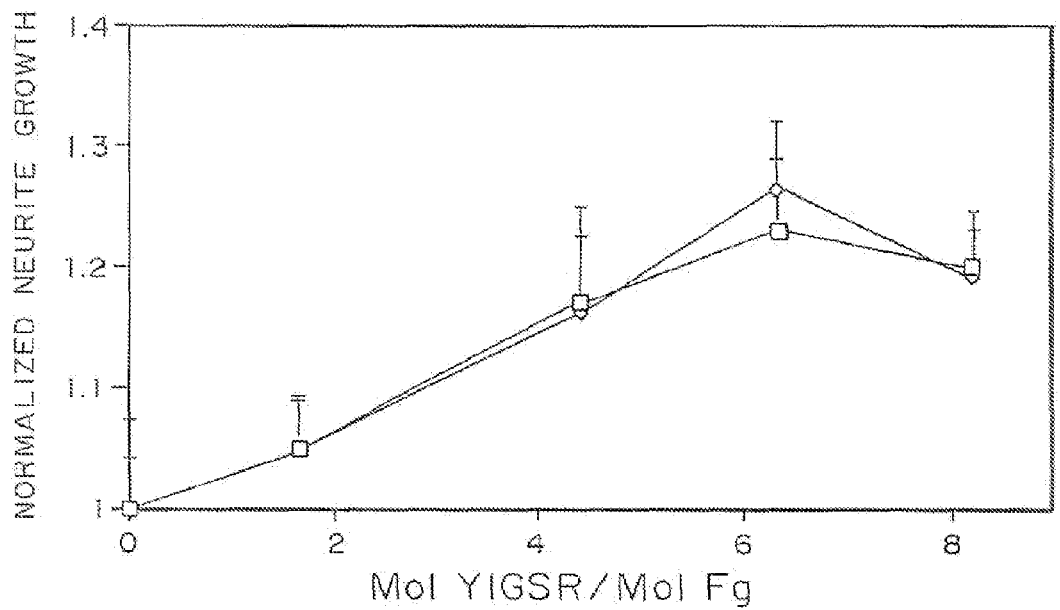

The biological effect of incorporated peptides in a three dimensional matrices demonstrated in the present example. Multiple peptide sequences from extracellular matrix proteins have been chosen. These proteins were chosen in part because of their reported ability to enhance neurite outgrowth (Yamada, 1991, Tashiro, et al., 1989). These proteins have been tested at various concentrations. To test these peptides, specific selected peptide sequences were cross-linked into a three dimensional fibrin matrix with a day 8 dorsal root ganglia embedded into the gels. The neurites were grown for 48 hr, and the migration rate of the neurties extending from the ganglia was quantified for each condition at both 24 and 48 hr. This growth was then normalized to the growth in unmodified fibrin. The ability for some of these peptides to enhance neurite outgrowth was found to increase with peptide concentration, while other peptides reach a maximal enhancement at a moderate peptide concentration. Two peptides that were tested, one from N-Cadherin, namely the tripeptide HAV (SEQ ID NO:6) (FIG. 1), and one which is present in many extracellular matrix proteins, namely RGD (SEQ ID NO:2) (FIG. 2), were shown to reach a maximal effect at a moderate concentration of incorporated peptide. HAV (SEQ ID NO:6) achieved a maximal effect at 2 mol/mol fg while RGD (SEQ ID NO:2) achieved a maximal effect at 1.5 mol/mol fg of incorporated peptide. In contrast, the peptide sequences IKVAV (SEQ ID NO:1) (FIG. 3), RNIAEIIKDI (SEQ ID NO:5) (FIG. 4) and YIGSR (SEQ ID NO:3) (FIG. 5) were shown to have a linear correlation between peptide concentration and the level of enhancement. YIGSR (SEQ ID NO:3), IKVAV (SEQ ID NO:1) and RNIAEIIKDI (SEQ ID NO:5) showed maximal enhancement at 6, 8 and 8 mol peptide/mol fibrinogen respectively.

EXAMPLE 2

Fibrin Gels With Multiple Peptides

Because two of the peptides that were tested were found to have maximal effect on the neuronal cell model employed at low concentrations, it is possible to incorporate these peptides at a low concentration and still observe a large neuronal effect, leaving many cross-linking sites open. The remaining sites can then be occupied with a different peptide which has it's maximal effect at a high concentration.

Figure 6:
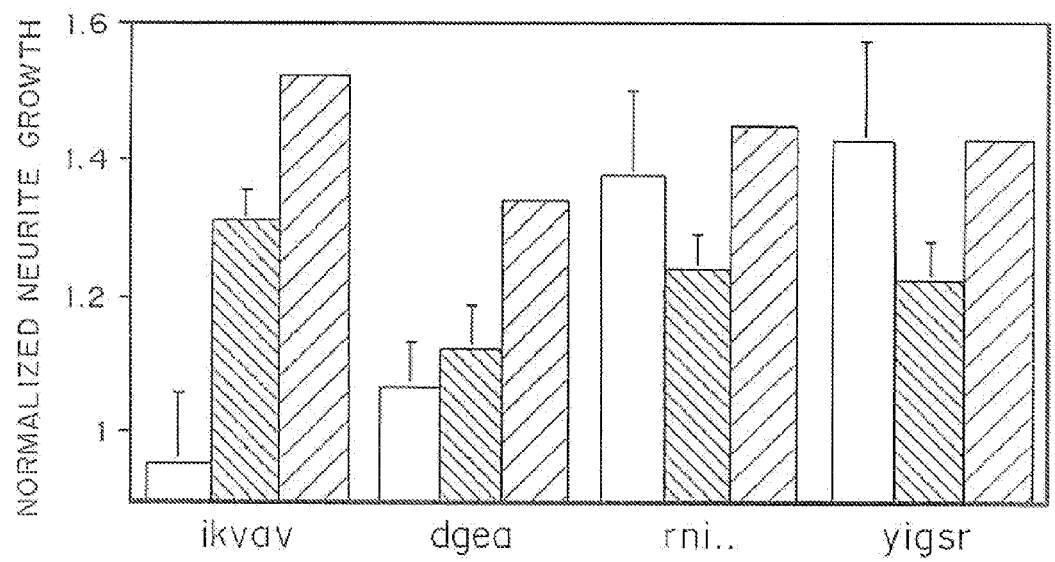

The present inventors employed the above approach using with several peptides. In one example, HAV (SEQ ID NO:6) was cross-linked at 2 mol/mol fibrinogen in combination with the following peptides at 6 mol/mol fibrinogen: IKVAV (SEQ ID NO:1), RNIAEIIKDI (SEQ ID NO:5), YIGSR (SEQ ID NO:3) and DGEA (SEQ ID NO:4). The growth obtained with the peptides grafted together, with the peptide grafted alone and the theoretical sum derived from the results of the two peptides grafted separately is shown in FIG. 6. The cross-linking of HAV (SEQ ID NO:6) with IKVAV (SEQ ID NO:1) results in a negative interaction, where the effect on neuronal outgrowth is lower than when IKVAV (SEQ ID NO:1) is grafted alone. The cross-linking of HAV (SEQ ID NO:6) with DGEA (SEQ ID NO:4) had relatively little to no additional effect on neurite extension, resulting in growth similar to when DGEA (SEQ ID NO:4) is cross-linked into the fibrin alone. The cross-linking of HAV (SEQ ID NO:6) with YIGSR (SEQ ID NO:3) has an additive effect on neurite extension.

In another example, RGD (SEQ ID NO:2) was cross-linked at 2 mol/mol fibrinogen with the same series of peptides at 6 mol/mol fibrinogen. In several examples, the effect was similar. The incorporation of RGD (SEQ ID NO:2) with IKVAV (SEQ ID NO:1) seemed to have a negative effect as the level of neurite outgrowth was similar to that in fibrin. When RGD (SEQ ID NO:2) was cross-linked with RNIAEIIKDI (SEQ ID NO:5), it has a neutral effect in that neurite growth was similar to that seen in gels modified with RNIAEIIKDI (SEQ ID NO:5) alone. Once again, grafting with YIGSR (SEQ ID NO:3) appeared to lead to an additive effect on neurite outgrowth.

Figure 7:
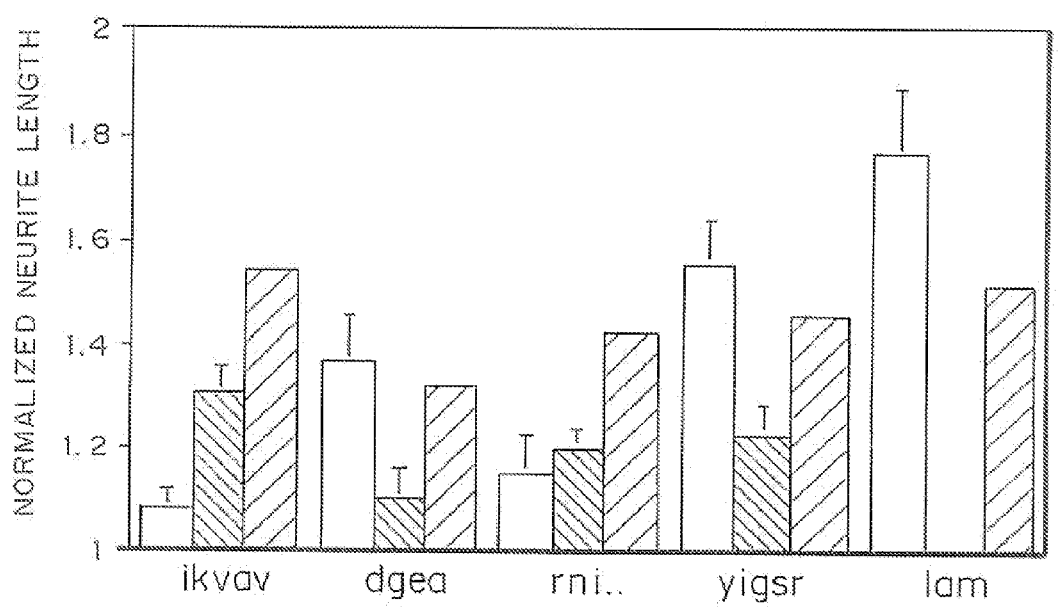
FIG. 7 Peptides were grafted in combination at a total concentration of 8 mol peptide/mol fg. RGD (SEQ ID NO:2) demonstrated a maximum efficacy at 2 mol/mol fg. Therefore, RGD (SEQ ID NO:2) was incorporated at this concentration and the second peptide shown was incorporated at 6 mol.mol fg. The growth of neurites relative to growth in unmodified fibrin is shown in the first bars of this graph. The normalized growth of the second peptide grafted alone is shown as well as the theoretical additive growth derived from the two peptides grafted alone. The final series of data labeled laminin represents the four relevant laminin derived peptides, RGD (SEQ ID NO:2), IKVAV (SEQ ID NO:1), RNIAEIIKDI (SEQ ID NO:5) and YIGSR (SEQ ID NO:3), these peptides were grafted in equimolar quantities at 2 mol peptide/mol fg. Mean and standard error of the mean are shown. Legend to FIG. 7: □ Grafted with RGD SEQ ID NO. NO:2), ▧ Sample Grafted Alone, ▨ Cumulative Value for Sample and RGD (SEQ ID NO:2).

One study was done where the four peptides derived from laminin were cross-linked into the fibrin at equimolar concentrations. Since 8 mol peptide/mol fibrinogen can be obtained, this material then had 2 mol/mol fibrinogen of IKVAV (SEQ ID NO:1), RGD (SEQ ID NO:2), YIGSR (SEQ ID NO:3), and RNIAEIIKDI (SEQ ID NO:5). When neutites were grown in this material, the effect led to 75% improvement, which was higher than the combined effects from the peptides grafting alone. These peptides were thus demonstrated in the present studies to act synergistically when co-grafted into fibrin. (FIG. 7)

By utilizing a peptide-modified fibrin matrix, a novel method has been developed that employs several active peptides in 3 dimensions. It is shown that the addition of protease inhibitors has no effect on 2-dimensional neurite outgrowth, but that addition of these same inhibitors decreases neurite outgrowth 3-dimensionally (Herbert, et al., 1996). Therefore, it becomes impossible to predict the activity of these peptides in 3 dimensions from the 2-dimensional model, because the effect of proteolysis often becomes the limiting factor for 3-dimensional migration.

Bi-domain peptides containing both a factor XIIIa substrate and a heparin-binding domain (Table 2) were synthesized and cross-linked into fibrin gels as previously demonstrated with one variation.

Table 2 Exact sequences of bi-domain peptides containing the factor XIIIa substrate sequence and the heparin binding domain sequence. The source for each heparin binding domain is shown as well.

TABLE 2

| Peptide Name | Sequence | Source |
|---|---|---|
| ATIII | LNQEQVSP K(βA)FAKLAARLYRKA (SEQ ID NO:18) | Antithrombin III |
| NCAM | LNQEQVSP YKKIIKKL (SEQ ID NO:19) | Neural cell adhesion molecule |
| PF4 | LNQEQVSP KHKGRDVILKKDVR (SEQ ID NO:20) | Platelet factor 4 |

(italics denote factor XIIIa substrate.)

Figure 8:
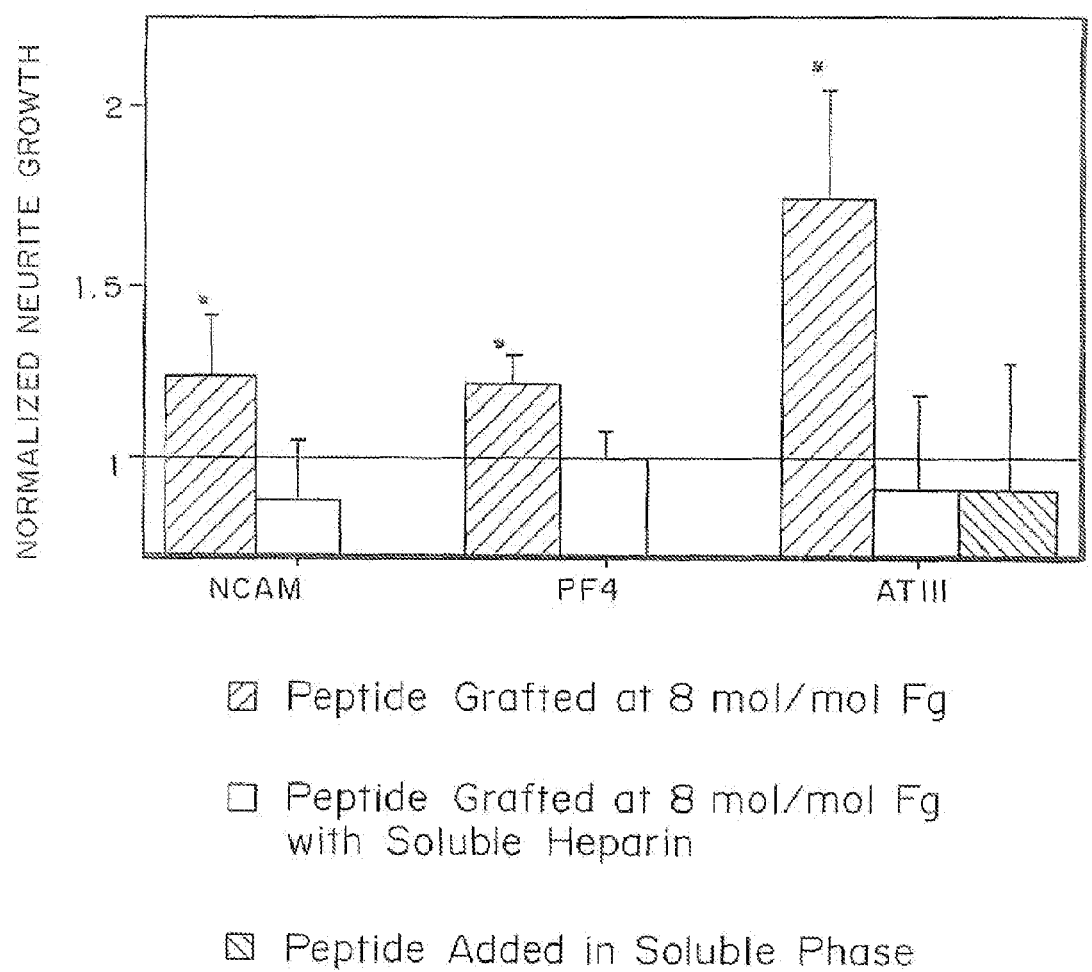
FIG. 8 Heparin binding peptides derived from three separate proteins, NCAM, platelet factor 4 and antithrombin III were cross-linked into fibrin at 8 mol/mol fg. The level of neurite outgrowth at 48 hours was normalized against growth in unmodified fibrin and is shown below. Additionally, controls of crosslinked peptide with heparin or just soluble peptide were tested. The growth is shown below with levels that are significantly different from unmodified fibrin (p<0.05) noted with a star. Mean and standard error of the mean are shown. Legend for FIG. 8: ▨ Peptide Grafted at 8 mol/mol Fg, □ Peptide Grafted at 8 mol/mol Fg with Soluble Heparin, ▧ Peptide Added in Soluble Phase.

In one example, the peptide was cross-linked into the gel alone and in the second example, it was incorporated in the presence of heparin. These two methods led to gels where an identical concentration of bi-domain peptide was covalently bound to the fibrin, but the first example resulted in free heparin binding domains being present in the gel, while the addition of heparin in the example condition resulted in this domain being occupied with a heparin fragment. Therefore, the effects of interaction between the growing neurites and either a heparin binding domain or heparin itself could be determined. When the peptide was incorporated without heparin present, it was able to enhance the extension of neurites from day 8 chick dorsal root ganglia. Three bi-domain peptides, each with a different heparin binding domain, were tested and gave statistically better growth than unmodified fibrin (FIG. 8). The level of improvement ranged from 75% to 25%. This level of enhancement could be correlated to the binding affinity of the heparin binding domain that was incorporated (Table 3). When heparin was added at the beginning of the study, it was discovered that this abolished the effect, resulting in growth similar to that seen in unmodified fibrin.

Table 3 Provides results of the relative heparin binding affinity and enhancement of three dimensional neurite outgrowth for several heparin binding peptides. There is a correlation between the binding strength for each peptide and the present enhancement of neurite outgrowth.

TABLE 3

| Peptide Name | Elution from Heparin Affinity Column (Mol NaCl) | Enhancement of Neurite Outgrowth (%) |
|---|---|---|
| ATIII (SEQ ID NO: 18) | 0.67 | 73.1 |
| NCAM (SEQ ID NO: 19) | 0.35 | 24.5 |
| PF4 (SEQ ID NO: 20) | 0.34 | 20.2 |

EXAMPLE 3

Custom-Designed Gel Matrix for Neurite Growth

There are four components necessary for creating a cross-linked fibrin gel; fibrinogen, calcium, thrombin and factor XIIIa, and the structural characteristics of the material. These four components can be modified by changing the concentration of any one of them. There are two main characteristics that determine the structure of the fibrin; the density of the fibrin bundles and the thickness of each individual bundle. These two properties will then control the ability of cells to infiltrate the matrix.

Increasing fibrin concentration from 5-15 mg/mL in the precursor mixture was found to result in fibrin gels with smaller fibrin bundles that are much denser. This resulting material has been shown to be more difficult for neurties to migrate through. When the calcium concentration was increased from 2-10 mM, the fibrin bundles got thicker, but the spacing between these bundles became greater. Changing the fibrin density clearly can have a direct effect on cellular migration while changes in the fibril morphology does not. Degradation of the fibrin matrix is dependent on the morphology of these fibers. Therefore, the ability for cells to infiltrate the fibrin and the overall degradation of the gel can be controlled independently. The kinetics of fibrin formation are dependent on the amount of the two enzymes, thrombin and factor XIII, that are present. Increasing the concentration of thrombin decreases time for gelatin while increasing the factor XIII concentration increases the rate of cross-link formation. By varying the concentrations of these four precursor components, the fibrin morphology and kinetics are manipulated to provide a matrix with optimal properties.

The present example demonstrates methods to control the cell-mediated rate of fibrin degradation. One method to control the degradation of the material is to modify the structural characteristics through the initial concentration of the precursor components. By making a fibrin gel that is denser, the rate of cellular infiltration, and related cellular degradation will be decreased. This can be accomplished by increasing the density of the gel through either an increase in the fibrinogen concentration or an increase in the cross-linking through the amount of factor XIIIa.

Another example involves controlling the rate of degradation by crosslinking exogenous protease inhibitors into the fibrin gel. In order to maximize the efficacy of these inhibitors, they must be covalently bound to the gel to provide a high local concentration. Therefore, proteases will be either selected or engineered to have a factor XIIIa substrate site. In the example of 2-plasmin inhibitor, a substrate sequence is already present. For other proteins, like aprotinin, this site in some embodiments of the invention will be built into the protein. These proteins will then be added to the coagulation mixture and allowed to cross-link into the fibrin. The inhibitors will remain in the gel through this covalent cross-link until enzymatic degradation of the fibrin begins. This initial degradation will then release the bound inhibitors, preventing widespread degradation of the fibrin matrix. This method can also be further modified to incorporate a enzymatic degradation site in the protease inhibitor between the cross-linking domain and the active protein domain. This method will then allow the protease inhibitor to be released free of fibrin degradation products, potentially increasing the efficacy of the released inhibitor.

Another example involves cross-linking bi-domain peptides into the fibrin that include a factor XIIIa substrate sequence and a protease binding domain. The binding domain in the peptide could be a degradation site that was selected to have a low Km and a low Kcat leading to high level of enzyme binding at the site but a low level of enzymatic activity. This would then serve to allow the incorporated peptides to act as a competitive inhibitor for fibrin degradation sites. However, since the incorporated peptide would be cleaved at a very slow rate, ti would effectively immobilize the protease and prevent it from degrading the fibrin matrix. Additionally, the binding domain could interact with the protease through a site unrelated to the enzymatic activity. (i.e. heparin binding) This would then allow the protease to be sequestered in the fibrin before ti could degrade the gel as well.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extend that they provide exemplary procedural or other details supplementary to those set forth herein, are specifically incorporated herein by reference.

1. Massia, S. P. et al, (1991). *Journal of Cell Biology* 114:1089-1100.
2. Yamada, K. M. (1991). *Journal of Biological Chemistry* 266:12809-12812.
3. DiMilla, P. A., et al, (1991). *Biophysics Journal* 60:15-37.
4. Tashiro K., et al, (1989). *Journal of Biological Chemistry* 264:16174-16182.
5. Martin, G. R. (1987). *Annual Review of Cellular Biology* 3:57-85.
6. Kleinman, H. K., et al, (1993). *Vitamins and Hormones* 47:10-93.
7. Edgar D, et al, (1984). *EMBO* 3:1463-1468.
8. Borrajo A, et al, (1997). *Bioorganic and Medicinal Chemistry Letters* 7:1185-1190.
9. Kallapur, S., et al, (1992). *Journal of Neuroscience Research* 33:538-548.
10. Kaneda N., et al, (1996). *Journal of Biochemistry* 119:1150-1156.
11. Rogers S., et al, (1985). *Journal of Neuroscience* 5:369-378.
12. Herbert, C. B., et al, (1996). *Journal of Comparative Neurology* 365:380-391.
13. Herbert, C. B., (1998). *J Biomed Mater Res* 40:551-559.

What is claimed is:

1. A protein matrix comprising a peptide comprising at least two domains, wherein
   the first domain comprises a protease inhibitor or a protease binding domain and
   the second domain comprises a substrate for a transglutaminase,
   wherein the peptide is cross-linked to the matrix by the second domain, and
   wherein the peptide is a chimeric peptide.

2. The matrix of claim 1, wherein the peptide comprises a first domain comprising aprotinin or antithromibin.

3. The matrix of claim 2, wherein the matrix is fibrin.

4. A peptide or protein comprising at least two domains, wherein the first domain comprises a protease inhibitor or protease binding domain and wherein the second domain comprises a substrate for a transglutaminase, wherein the peptide or protein is covalently attachable to a matrix through the second domain, and
   wherein the peptide or protein is a chimeric peptide or protein.

5. The peptide or protein of claim 4, wherein the first domain comprises aprotinin.

6. The peptide or protein of claim 4, wherein the first domain comprises antithrombin III.

7. The peptide or protein of claim 4, further comprising a degradation site between the first domain and the second domain.

8. The peptide or protein of claim 4, wherein the transglutaminase is factor XIIIa.

9. The peptide or protein of claim 4, wherein the first domain comprises a protease inhibitor.

10. The peptide or protein of claim 4, wherein the first domain comprises a protease binding domain.

11. The peptide or protein of claim 10, comprising a degradation site.

12. The peptide or protein of claim 11, wherein the degradation site is in the protease binding domain.

* * * * *

SEQUENCE LISTING

<160> NUMBER OF SEQ ID NOS: 20

<210> SEQ ID NO 1
<211> LENGTH: 5
<212> TYPE: PRT
<213> ORGANISM: artificial sequence
<220> FEATURE:
<223> OTHER INFORMATION: heparin binding peptide

<400> SEQUENCE: 1

Ile Lys Val Ala Val
1               5

<210> SEQ ID NO 2
<211> LENGTH: 3
<212> TYPE: PRT
<213> ORGANISM: artificial sequence
<220> FEATURE:
<223> OTHER INFORMATION: heparin binding peptide

<400> SEQUENCE: 2

Arg Gly Asp
1

<210> SEQ ID NO 3

```
<211> LENGTH: 5
<212> TYPE: PRT
<213> ORGANISM: artificial sequence
<220> FEATURE:
<223> OTHER INFORMATION: heparin binding peptide

<400> SEQUENCE: 3

Tyr Ile Gly Ser Arg
1               5

<210> SEQ ID NO 4
<211> LENGTH: 4
<212> TYPE: PRT
<213> ORGANISM: artificial sequence
<220> FEATURE:
<223> OTHER INFORMATION: heparin binding peptide

<400> SEQUENCE: 4

Asp Gly Glu Ala
1

<210> SEQ ID NO 5
<211> LENGTH: 10
<212> TYPE: PRT
<213> ORGANISM: artificial sequence
<220> FEATURE:
<223> OTHER INFORMATION: heparin binding peptide

<400> SEQUENCE: 5

Arg Asn Ile Ala Glu Ile Ile Lys Asp Ile
1               5                   10

<210> SEQ ID NO 6
<211> LENGTH: 3
<212> TYPE: PRT
<213> ORGANISM: artificial sequence
<220> FEATURE:
<223> OTHER INFORMATION: heparin binding peptide

<400> SEQUENCE: 6

His Ala Val
1

<210> SEQ ID NO 7
<211> LENGTH: 4
<212> TYPE: PRT
<213> ORGANISM: Artificial sequence
<220> FEATURE:
<223> OTHER INFORMATION: heparin binding peptide

<400> SEQUENCE: 7

Asn Cys Ala Met
1

<210> SEQ ID NO 8
<211> LENGTH: 14
<212> TYPE: PRT
<213> ORGANISM: artificial sequence
<220> FEATURE:
<223> OTHER INFORMATION: heparin binding sequence
<220> FEATURE:
<221> NAME/KEY: MISC_FEATURE
<222> LOCATION: (2)..(2)
<223> OTHER INFORMATION: beta-alanine

<400> SEQUENCE: 8

Lys Ala Phe Ala Lys Leu Ala Ala Arg Leu Tyr Arg Lys Ala
1               5                   10
```

```
<210> SEQ ID NO 9
<211> LENGTH: 8
<212> TYPE: PRT
<213> ORGANISM: artificial sequence
<220> FEATURE:
<223> OTHER INFORMATION: heparin binding peptide

<400> SEQUENCE: 9

Tyr Lys Lys Ile Ile Lys Lys Leu
1               5

<210> SEQ ID NO 10
<211> LENGTH: 14
<212> TYPE: PRT
<213> ORGANISM: artificial sequence
<220> FEATURE:
<223> OTHER INFORMATION: heparin binding sequence

<400> SEQUENCE: 10

Lys His Lys Gly Arg Asp Val Ile Leu Lys Lys Asp Val Arg
1               5                   10

<210> SEQ ID NO 11
<211> LENGTH: 19
<212> TYPE: PRT
<213> ORGANISM: artificial sequence
<220> FEATURE:
<223> OTHER INFORMATION: heparin binding sequence

<400> SEQUENCE: 11

Tyr Glu Lys Pro Gly Ser Pro Pro Arg Glu Val Val Pro Arg Pro Arg
1               5                   10                  15

Pro Cys Val

<210> SEQ ID NO 12
<211> LENGTH: 15
<212> TYPE: PRT
<213> ORGANISM: artificial sequence
<220> FEATURE:
<223> OTHER INFORMATION: heparin binding sequence

<400> SEQUENCE: 12

Lys Asn Asn Gln Lys Ser Glu Pro Leu Ile Gly Arg Lys Lys Thr
1               5                   10                  15

<210> SEQ ID NO 13
<211> LENGTH: 6
<212> TYPE: PRT
<213> ORGANISM: artificial sequence
<220> FEATURE:
<223> OTHER INFORMATION: heparin binding sequence

<400> SEQUENCE: 13

Lys Asp Pro Lys Arg Leu
1               5

<210> SEQ ID NO 14
<211> LENGTH: 6
<212> TYPE: PRT
<213> ORGANISM: artificial sequence
<220> FEATURE:
<223> OTHER INFORMATION: heparin binding sequence

<400> SEQUENCE: 14

Tyr Arg Ser Arg Lys Tyr
```

```
<210> SEQ ID NO 15
<211> LENGTH: 6
<212> TYPE: PRT
<213> ORGANISM: artificial sequence
<220> FEATURE:
<223> OTHER INFORMATION: heparin binding sequence

<400> SEQUENCE: 15

Tyr Lys Lys Pro Lys Leu
1               5

<210> SEQ ID NO 16
<211> LENGTH: 7
<212> TYPE: PRT
<213> ORGANISM: artificial sequence
<220> FEATURE:
<223> OTHER INFORMATION: heparin binding sequence

<400> SEQUENCE: 16

Ala Lys Arg Ser Ser Lys Met
1               5

<210> SEQ ID NO 17
<211> LENGTH: 6
<212> TYPE: PRT
<213> ORGANISM: artificial sequence
<220> FEATURE:
<223> OTHER INFORMATION: heparin binding sequence

<400> SEQUENCE: 17

Cys Arg Lys Arg Cys Asn
1               5

<210> SEQ ID NO 18
<211> LENGTH: 22
<212> TYPE: PRT
<213> ORGANISM: artificial sequence
<220> FEATURE:
<223> OTHER INFORMATION: a peptide chimera containing both a factor
      XIIIa substrate and a heparin-binding domain
<220> FEATURE:
<221> NAME/KEY: MOD_RES
<222> LOCATION: (1)..(1)
<223> OTHER INFORMATION: dansyl leucine
<220> FEATURE:
<221> NAME/KEY: MOD_RES
<222> LOCATION: (10)..(10)
<223> OTHER INFORMATION: beta alanine

<400> SEQUENCE: 18

Leu Asn Gln Glu Gln Val Ser Pro Lys Ala Phe Ala Lys Leu Ala Ala
1               5                   10                  15

Arg Leu Tyr Arg Lys Ala
            20

<210> SEQ ID NO 19
<211> LENGTH: 16
<212> TYPE: PRT
<213> ORGANISM: artificial sequence
<220> FEATURE:
<223> OTHER INFORMATION: heparin binding sequence
<220> FEATURE:
<221> NAME/KEY: MOD_RES
<222> LOCATION: (1)..(1)
<223> OTHER INFORMATION: dansyl leucine

<400> SEQUENCE: 19
```

```
Leu Asn Gln Glu Gln Val Ser Pro Tyr Lys Lys Ile Ile Lys Lys Leu
1               5                   10                  15

<210> SEQ ID NO 20
<211> LENGTH: 22
<212> TYPE: PRT
<213> ORGANISM: artificial sequence
<220> FEATURE:
<223> OTHER INFORMATION: heparin binding sequence
<220> FEATURE:
<221> NAME/KEY: MOD_RES
<222> LOCATION: (1)..(1)
<223> OTHER INFORMATION: dansyl leucine

<400> SEQUENCE: 20

Leu Asn Gln Glu Gln Val Ser Pro Lys His Lys Gly Arg Asp Val Ile
1               5                   10                  15

Leu Lys Lys Asp Val Arg
            20
```